United States Patent [19]

Washida et al.

[11] Patent Number: 5,625,039
[45] Date of Patent: Apr. 29, 1997

[54] ANTI-HUMAN IGE MONOCLONAL ANTIBODIES

[75] Inventors: Naohiro Washida; Toshiko Yoshida, both of Tochigi, Japan

[73] Assignee: Snow Brand Milk Products Co., Ltd., Hokkaido, Japan

[21] Appl. No.: 336,569

[22] Filed: Nov. 9, 1994

Related U.S. Application Data

[63] Continuation of Ser. No. 994,503, Dec. 21, 1992, abandoned.

[30] Foreign Application Priority Data

Dec. 24, 1991 [JP] Japan ..................................... 3-357005

[51] Int. Cl.$^6$ .................................................. C07K 16/42
[52] U.S. Cl. .............................. 530/388.25; 530/388.73
[58] Field of Search ........................ 530/388.25, 388.73; 435/240.27, 172.2, 70.21

[56] References Cited

U.S. PATENT DOCUMENTS 4,714,759 12/1987 Whitaker, Jr. .
4,940,782 7/1990 Rup et al. ........................... 530/388.25

FOREIGN PATENT DOCUMENTS 0205405 12/1986 European Pat. Off. .
0396505 11/1990 European Pat. Off. .
0403312 12/1990 European Pat. Off. .
WO89/04834 6/1989 WIPO .
8906138 7/1989 WIPO .

OTHER PUBLICATIONS

Hook et al. Fed Proc 46:1346, 1987.
The Embo Journal, vol. 4, No. 13B, 1985, Oxford England, pp. 3681–3688, Ollier et al., – "The Idiotypic Network and the Internal Image:Possible Regulation . . . in the Gat System".
The Embo Journal, vol. 5, No. 7, 1986, Oxford England, pp. 1577–1587, Caton et al., –"Structural and Functional Implications of a Restricted Antibody Response to a Defined Antigenic Region . . . Virus Hemagglutinin".
Bio/Technology, vol. 8, Feb. 1990, New York, USA, pp. 122–126, Chang et al., – "Monoclonal Antibodies Specific for Human IgE–Producting B Cells: A Potential Therapeutic . . . Allergic Diseases".
Nakajima et al. Allergy 44:187–191, 1989.
Chang et al., Biotechnology 8:122–127, 1990.
Vercelli et al. Nature 338:649–651, 1989.
Kabat et al. "Sequences of Proteins of Immunological Interest", 5th Edition US Dept. HHS pp. 163–200, 1991.

*Primary Examiner*—Toni R. Scheiner
*Attorney, Agent, or Firm*—Burgess, Ryan & Wayne

[57] ABSTRACT

Monoclonal antibodies are provided which specifically bind to human immunoglobulin e (IgE) and has a molecular weight of approximately 150,000 determined by SDS-polyacrylamide gel electrophoresis (non-reduced state), the ability to bind to human IgE-producing B cells, the ability to recognize IgE bound to human or canine cell having Fcε receptor and further characterized by specific sequences.

1 Claim, 7 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 17
        ( B ) TYPE: AMINO ACID
        ( C ) STRANDEDNESS:
        ( D ) TOPOLOGY: LINEAR ( x i ) SEQUENCE DESCRIPTION: SEQ ID NO:1:

```
Asp Ile Val Leu Thr Gln Ser Pro Ala Ser Leu Ala Val Ser Leu
 1               5                  10                  15
Gly Gln
```

( 2 ) INFORMATION FOR SEQ ID NO:2:

( i ) SEQUENCE CHARACTERISTICS:
        ( A ) LENGTH: 22
        ( B ) TYPE: AMINO ACID
        ( C ) STRANDEDNESS:
        ( D ) TOPOLOGY: LINEAR ( x i ) SEQUENCE DESCRIPTION: SEQ ID NO:2:

```
Asp Ile Val Leu Thr Gln Ser Pro Ala Ser Leu Ala Val Ser Leu
 1               5                  10                  15
Gly Gln Arg Ala Thr Ile Ser
                 20
```

( 2 ) INFORMATION FOR SEQ ID NO:3:

( i ) SEQUENCE CHARACTERISTICS:
        ( A ) LENGTH: 19
        ( B ) TYPE: AMINO ACID
        ( C ) STRANDEDNESS:
        ( D ) TOPOLOGY: LINEAR ( x i ) SEQUENCE DESCRIPTION: SEQ ID NO:3:

```
Asp Val Val Met Thr Gln Thr Pro Leu Ser Leu Pro Val Ser Leu
 1               5                  10                  15
Gly Asp Gln Ala
```

( 2 ) INFORMATION FOR SEQ ID NO:4:

( i ) SEQUENCE CHARACTERISTICS:

(A) LENGTH: 20
(B) TYPE: AMINO ACID
(C) STRANDEDNESS:
(D) TOPOLOGY: LINEAR (xi) SEQUENCE DESCRIPTION: SEQ ID NO:4:

```
Asp Val Val Met Thr Gln Thr Pro Leu Ser Leu Pro Val Ser Leu
 1               5                  10                   15
Gly Asp Gln Ala Ser
                 20
```

ANTI-HUMAN IGE MONOCLONAL ANTIBODIES

This application is a continuation of application Ser. No. 07/994,503 filed Dec. 21, 1992, now abandoned.

BACKGROUND OF THE INVENTION

1. Field of the Invention

This invention relates to new monoclonal antibodies having a specific binding property to human immunoglobulin E (IgE) and useful for the treatment of allergic diseases.

2. Description of Prior Art

Immune reaction is a defensive mechanism of a living body to protect against the invasion of foreign microorganisms from outside of the body such as an infection. This mechanism may affect the living body and is generally called an allergy. Recently, allergic rhinitis caused by the pollen of *Cryptomeria japonica* has been the focus of attention. Allergy is classified into types I to IV with its occurring processes. Type I allergy is a typical allergy known as immediate-type allergy and generally called allergy. The type I allergy is mediated by immunoglobulin E (IgE) and the immune response caused by IgE antibody starts by the following mechanisms.

First, IgE binds to Fcε receptor on mast cells in tissue or basophils in the blood, then an antigen binds to a recognition site in the antibody to form a cross-linked structure between IgE antibodies. Mast cells and basophils are stimulated by the cross-linkage and release various chemical mediators which cause a variety of allergic attacks such as asthma and edema.

Elucidation of the allergic response mechanism initiated studies to investigate medicines that act to IgE for the prevention and treatment of allergy. Particularly, IgE antibody has been tried for the treatment and prevention. For example, Japanese Un-examined Patent Publication No. 102032 (1989) discloses a treatment by anti-IgE antibody bound to a toxin to selectively attack cells having IgE antibody on their surfaces and eliminate IgE producing cells. On the other hand, it has been pointed that binding of these antibodies to IgE on the surfaces of mast cells and basophils to form cross-linked bridge of IgE antibodies on the cell surfaces causes to stimulate adversely the release of chemical mediators. Application of neutralizing antibody against IgE antibody also shows similar results. Japanese Un-examined Patent Publication Nos. 289100 (1986) and 127977 (1991) disclose the prevention and treatment of allergy by the use of an monoclonal antibody to Fcε receptor which specifically binds to IgE to inhibit the binding of IgE antibody to mast cells and basophils. Chang et al. reported a treatment of allergy by inhibiting the binding of IgE antibody to such cells using an antibody to Fc in IgE antibody (T. W. Chang et al., BIO/TECHNOLOGY, vol. 8, 122–126, (1990)).

Hardly any practical treatment of allergic diseases with monoclonal antibody to IgE antibody has been reported.

Japanese Un-examined Patent Publication No. 72500 (1991) discloses a monoclonal antibody which does neither recognize IgE bound to Fcε receptor nor stimulate the release of mediators from cells as a new anti-IgE antibody. Inhibition of histamine release from mast cells derived from human peripheral blood by the treatment with the monoclonal antibody after sensitization with IgE has been confirmed.

SUMMARY OF THE INVENTION

The object of the invention is to provide novel anti-human IgE monoclonal antibodies which dissociate IgE antibody from the surface of mast cells and basophils, and to inhibit histamine release by antigen stimulation. The N-terminal amino acid sequences in the L-chain of the monoclonal antibody were identified and clearly different from those of known antibodies.

The novel monoclonal antibodies provided by the present invention have the following characteristic features:

① Molecular weights are approximately 150,000 determined by SDS-polyacrylamide gel electrophoresis (SDS-PAGE) (non-reduced state).
② The isotypes of antibodies are IgG2a or IgG2b.
③ The antibodies bind to human IgE-producing B cells.
④ The antibodies bind to IgE on the IgE-producing B cells.
⑤ The antibodies recognize IgE bound to human and canine cells having Fcε receptor.
⑥ The N-terminal amino acid sequences in the L-chain of the antibodies can be specified by one of sequence Nos. 1, 2, 3 and 4 in the Sequence list.
⑦ The antibodies competitively dissociate IgE antibody from Fcε receptor.
⑧ The antibodies do not induce the release of mediators from cells having Fcε receptor.

Any antibody having the above mentioned characteristic features can be used regardless of derived animal species and generally human and mouse type antibodies may be illustrated. Chimeric antibody, CDR grafted antibody and Fab fraction may also be included.

DETAILED DESCRIPTION OF PREFERRED EMBODIMENTS

Figure 1:
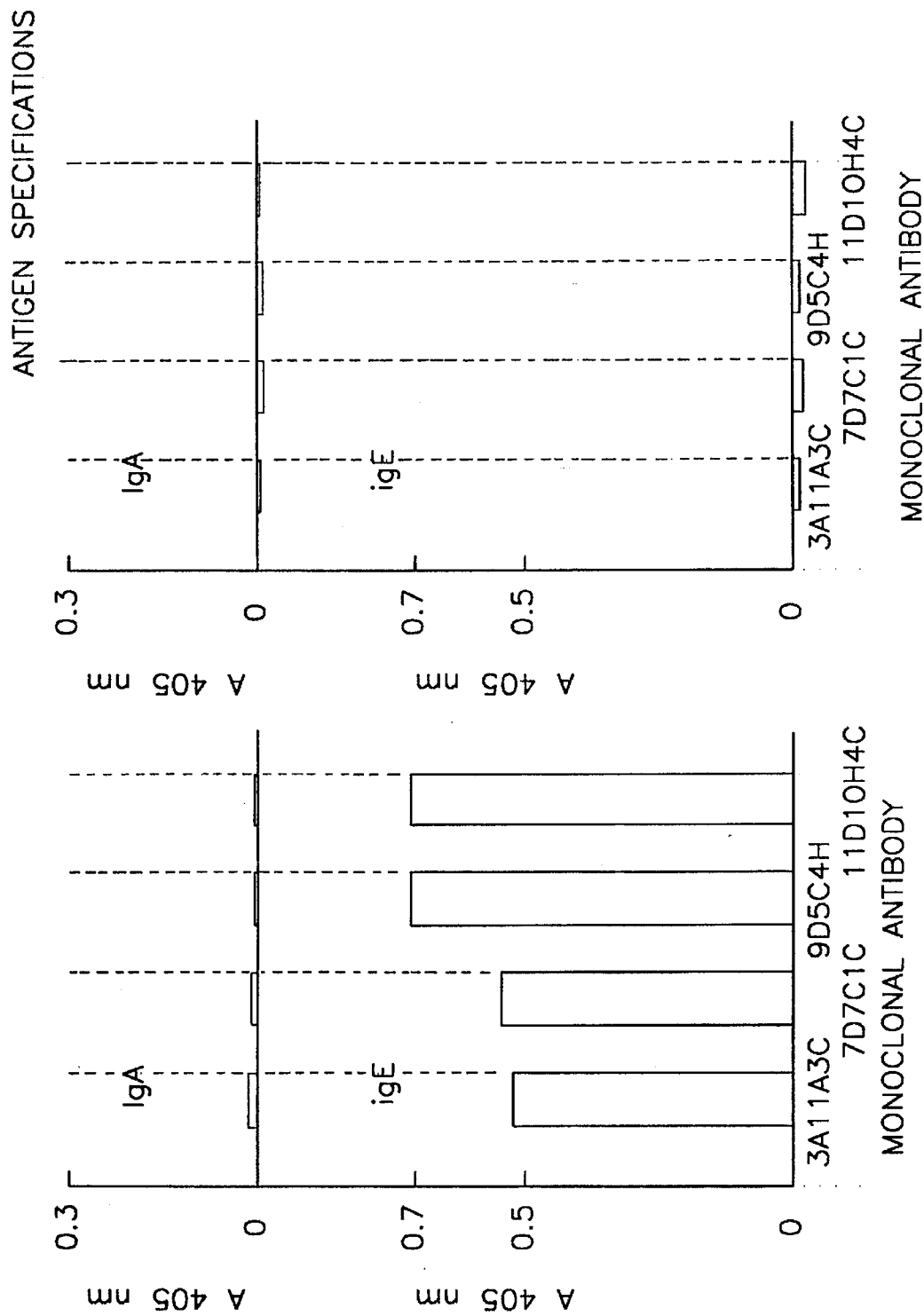
FIG. 1 shows the antigen specificities of the monoclonal antibodies of the present invention.

The antibodies of the present invention recognize IgE bound to Fcε receptors on the surface of mast cells and basophils which release chemical mediators, dissociate IgE from Fcε receptor and inhibit the release of chemical mediators from those cells. Furthermore, the antibodies bind to free IgE and IgE antibodies on B cell surface. The antibodies having such characteristic features can be obtained from numerous monoclonal antibodies by the screening disclosed only by the present invention.

The antibodies of the present invention can be produced by the following procedures:

(1) Preparation of Antigen

IgE antibody is used as an immunogen to prepare the antibody producing cells of the present invention. Human derived purified IgE antibody is preferably used to accomplish the object of the present invention. The purified IgE antibody can be prepared from sera of autoimmune disease patients or from culture supernatant of IgE-producing cells.

(2) Preparation of Hybridomas

An animal is immunized by intraperitoneal injection of IgE by known methods, then the spleen is excised and its cells are collected. In vitro immunization may also be applicable. The splenocytes thus obtained are fused with parent cells to give hybrid cells. P3-X63-Ag8, P3-X63-Ag8-U1, P3-NSI/1-Ag4-1, X63-Ag8-6.5.3, Sp2/0-Ag14 and F0 strains derived from mice are typically us ed as parent cells for cell fusion. Strains derived from rats such as 210.RCY.Ag 1.2.3, BW5147.G.1.4, and EL4.BU are also used. Human derived cell strains include SKO-007, GM1500 and 6TG-A11. Furthermore, cell strains derived from human such as immortalized cells by Epstein-Bart virus (EBV) may also be used.

Cell fusion is carried out by conventional methods and PEG, Sendai virus and electric pulse methods can be illustrated.

(3) Screening of Hybridoma

The screening of hybridomas which produce the desired monoclonal antibodies is performed by HAT selection method after cell fusion with X63-Ag8-6.5.3 strain disclosed later in the example of the present invention. Furthermore, hybridoma strain is screened to obtain cells producing the desired antibody by analysis of culture supernatants. Plaque assay, agglutination reaction, RIA or ELISA methods can be applied for the analysis of culture supernatants.

(4) Culture of hybridoma

The resultant hybridoma is generally transplanted into a mouse abdominal cavity and ascite fluid are recovered when the hybridomas were derived from mouse. Human derived cells are cultured in RPMI-1640 supplemented with 10% fetal bovine serum.

(5) Recovery of antibodies

The recovery of antibodies from culture supernatants or ascites is carried out by conventional methods. For example, ammonium sulfate fractionation, gel filtration, ion exchange chromatography and affinity chromatography can be used singly or in combination, if necessary.

(6) Characteristic Features of the Antibodies

The antibodies obtained by the present invention have following characteristic features confirmed by the methods shown below:

① Molecular weight.

The purified antibodies of the present invention show a molecular weight of about 150,000 in non-reduced condition by SDS-polyacrylamide gel electrophoresis (SDS-PAGE).

② Isotype analysis of the antibodies.

Subclasses of the purified antibodies are analyzed generally by ELISA method using corresponding antibodies. Isotyping Kit (Amarsham Co., Ltd. ) may be illustrative of the test kit. The isotypes of the antibodies of the present invention belong to IgG2a(κ) or IgG2b(κ).

③ Analysis of N-terminal Amino Acid Sequence in the Antibodies.

The antibodies can be identified by the analysis of N-terminal amino acid sequences. The analysis is performed by the separation of light chain (L-chain) and heavy chain (H-chain), followed by Edman degradation and stepwise determination of the respective N-terminal amino acid sequence. The sequence analysis using an amino acid sequencer can be performed by the following procedure.

The antibody is dissolved in 10 mM Tris HCl buffer (pH 8) containing 1 mM EDTA, 2.5% SDS, 0.01% bromophenol blue, 10% 2-mercaptoethanol and 10% glycerol and the resultant solution is heated at 100° C. for 3 minutes, centrifuged and the supernatant is recovered. The H- and L-chains are separated by an SDS polyacrylamide gel electrophoresis and electrically blotted on polyvinylidene difluoride membrane, stained with Coomassie Brilliant Blue. The membranes corresponding to the respective chain are cut out and analyzed with a protein sequencer.

The N-terminal amino acid sequence of L-chain is identified as one of the sequence Nos. 1, 2, 3 and 4 in the Sequence list.

④ Specific Properties of the Antibodies.

(a) Specificity of the Antibody.

The reactivities of the antibodies to IgE, IgG, IgM and IgA are determined by ELISA method using plates fixed class antibody. The antibodies of the present invention bind solely to IgE and no response is found with the other classes of antibodies.

(b) Binding to IgE-producing Cells.

The antibodies of the present invention bind to human IgE-producing B cells and are determined using a known IgE-producing myeloma cell line such as SKO-007 cell. Cultured cells are distributed into a microplate and the antibodies of the present invention are added and caused to react, thereafter, an antibody labeled with peroxidase (anti-mouse antibody was used in the example of the present invention) is added and the binding is determined by ELISA method.

(c) Antagonistic Action to IgE Antibody Bound to Fcε Receptor.

The antibodies of the present invention dissociate IgE antibody from Fcε receptor, which is bound to mast cells and basophils having the Fcε receptors. The antibodies of the present invention do not induce histamine release from these IgE bound cells.

Heparin added peripheral blood sample is drawn from a healthy human or dog, diluted to 2-fold with PBS and mononuclear cells are isolated. The isolated mononuclear cells fraction is used for the confirmation of the antibody activity of the present invention. Mononuclear cell fraction is washed with RPMI-1640 medium containing 10% FCS and treated with the antibodies of the present invention to measure the released histamine from cells. As a control, the sample is treated with goat anti-human IgE polyclonal antibody without addition of the antibody and its histamine concentration is determined similarly. Treatment with goat anti-human IgE polyclonal antibody induces a large amount of histamine release. However, the treatment with the antibodies of the present invention show declined release of histamine from cells than that without addition of the antibody, which indicate the dissociating activity of IgE antibody from Fcε receptor.

The antibodies of the present invention recognize human IgE antibody, thus the antibodies can be used for the treatment of allergic diseases singly or in combination with cytotoxins such as ricin, diphtheria toxin and methotrexate. Furthermore, a highly recognitive property to IgE allows selective isolation and analysis of IgE.

EXAMPLES

The present invention is further explained in detail by the following examples.

Example 1

Preparation of Anti-human IgE Antibody Producing Hybridoma (1) Preparation of Immunized Spleen Cells.

To BALB/c mouse, 10 μg of human IgE (Serotech Co., Ltd.) was intraperitoneally administered every week four times together with Freund's complete adjuvant and 10 μg of human IgE dissolved in PBS was injected intravenously as a final immunization. After three days, the spleen was aseptically excised from mouse and a single cell suspension was prepared using RFMI-1640 medium. Separately, mouse myeloma cells, X63-Ag8-6.5.3, were cultured by a conventional method using RPMI-1640 medium to fuse with the immunized cells mentioned above.

(2) Cell Fusion.

The mouse spleen cells prepared above and a mouse myeloma X63-Ag8-6.5.3 cells were mixed at a ratio of 5:1, centrifuged and supernatant was discarded. To the cells in the bottom of the centrifugal tube, RPMI-1640 medium containing 50% PEG4000 warmed at 37° C. was slowly added dropwise. PEG solution was diluted by mixing with 10 ml of FCS free RPMI-1640 medium. After dilution, the mixture was centrifuged and the supernatant was removed. The sedimented cells were diluted with RPMI-1640 medium containing 10% FCS to give $5-6 \times 10^6$ spleen cells/ml and distributed to a 96 well plate at a rate of 100 μl/well.

(3) Screening of Hybridoma.

HAT medium was added at day 4, 6, and 9 to the wells after the above mentioned fusion and cultured for 10–14 days. Above mentioned HAT medium was prepared by adding 100 μM of hypoxanthine, 0.1 μM of aminopterine, 1.6 μM of thymidine, $5 \times 10^{-5}$M of 2-mercaptoethanol, 100 U/ml of penicillin and 0.1 mg/ml of streptomycin to RPMI-1640 medium containing 10% FCS. The analysis of the culture supernatants was carried out by the following procedure.

(4) Preparation of Plate for Analysis.

In a 96 well plate (Falcon Co., Ltd.), 100 μl each of two μg/ml of human IgE (Serotech Co., Ltd.) was placed and allowed to stand overnight at 4° C., 2% bovine serum albumin (BSA) was added and allowed to stand for one hr. at room temperature, then the mixture was washed with 10 mM phosphate buffer (pH 7.4)—0.15M NaCl (PBS) to prepare plates for analysis.

(5) Screening of Hybridoma.

The supernatants of wells confirmed the cell growth were isolated and 100 μl each was added to the wells of the plate for the analysis shown above. The plate was allowed to s rand for two hrs., washed three times with PBS-0.05% Tween20 (PBS-Tween), 100 μl/well each of peroxidase-labeled goat anti-mouse immoglobulin (MBL Co., Ltd.) was added and incubated at 37° C. for two hrs. The wells were washed three times with PBS-Tween, added 200 μl/well each of a mixed solution of 20 ml of 0.1M sodium acetate-0.05M sodium dihydrogenphosphate buffer, 1.0 ml of 40 mM ABTS (2,2'-azino-di-(3-ethylbenzothiazolin sulfonate) and 0.2 ml of 0.25M hydrogen peroxide solution, prepared just before the addition, as a substrate for the determination of enzyme activity, and incubated at room temperature. After the reaction, the absorbance at 405 nm was measured with ImmunoReader NJ-2000 (Nippon InterMed Co. Ltd.).

Hybridoma cells secreting antibodies which specifically bind to human IgE were distributed into a 96 well plate at a rate of one cell/well, were cloned by limiting dilution method and chosen. The characteristics of antibodies were analyzed according to the methods in the following examples and selected four antibody-producing hybridomas suitable for the present invention and named 3A11A3C, 7D7C1C, 9D5C4H and 11D10H4C, respectively. The four hybridomas were deposited on Nov. 25, 1992 in the Agency of Industrial Science and Technology, Fermentation Research Institute as FERM BP-4075, 4076, 4077 and 4078, respectively. The Agency is located at 1–3, Higashi 1-chome, Tsukuba-shi, Ibaraki-ken 305, JAPAN.

(6) Culture of Hybridomas and Recovery of Antibody.

The obtained four hybridomas were incubated separately in RPMI-1640 medium supplemented with 10% FCS at 37° C. in an atmosphere containing 5% $CO_2$ and the antibodies were recovered from culture supernatants by ammonium sulfate precipitation.

Example 2

Production of Monoclonal Antibody.

BALB/c mouse was administered 0.5 ml of pristane (2,6,10,14-tetramethylpenfadecane) intraperitoneally. After 1–2 weeks, each of the hybridomas obtained by the Example 1 were intraperitoneally inoculated at a rate of $1 \times 10^7$ cells per mouse. The ascites was collected after 10–14 days.

The purification of monoclonal antibody in the ascites was performed using MAPS monoclonal antibody purification system (BioRad Co., Ltd.).

Example 3

Determination of Physicochemical Properties of the Monoclonal Antibody.

Four antibodies produced by clones obtained by the Example 1 were analyzed.

(1) Determination of Molecular Weight.

The molecular weight was determined by SDS-polyacrylamide gel electrophoresis (SDS-PAGE) using Laemmli's buffer. The molecular weights of the antibodies were determined by comparing the molecular weight marker (BioRad Co., Ltd.) and showed approximately 150,000 under non-reduced condition.

(2) Isotype Analysis of the Antibodies.

The analysis was performed using the isotyping kit (Amarsham Co., Ltd.). The isotypes of antibodies are shown in Table 1.

TABLE 1

| Isotypes of mouse anti-human IgE antibodies | |
| --- | --- |
| Antibody | Isotype |
| 3A11A3C | IgG2b(κ) |
| 7D7C1C | IgG2b(κ) |
| 9D5C4H | IgG2a(κ) |
| 11D10H4C | IgG2a(κ) |

(3) N-terminal Amino Acid Sequence

Purified antibody was dissolved in 10 mM Tris HCl buffer (pH 8) containing 1 mM EDTA, 2.5% SDS, 0.01% Bromophenol Blue, 10% 2-mercaptoethanol and 10% glycerol at a rate of two μg/μl. The resultant solution was heated at 100° C. for three minutes, centrifuged at 15,000 rpm for three minutes and the resultant supernatant solution was recovered. The recovered supernatant was subjected to SDS-polyacrylamide gel electrophoresis (10% gel) and the H- and L-chains were separated. The two chains were electrically blotted on to polyvinylidene difluoride membrane, stained with Coomassie Brilliant Blue, destained with 25% methanol solution containing 7% acetic acid and then dried in the air. The membranes corresponding to the chains were cut out, directly introduced in a vapor phase protein sequencer (Applied Biosystems Co., Ltd., Model 477A) and automatically subjected to coupling cleavage conversion using a program prepared in advance. The resultant PTH-amino acids were dissolved in 20% acetonitrile and injected in a reverse phase high performance liquid chromatography (Applied Biosystems Co., Ltd., Model 120A, column C-18, φ 2.1 mm×220 mm). The respective amino acid was identified by comparing the retention time with that of standard PTH amino acid. The N-terminal amino acid sequences of respective L-chain were shown below. The N-terminal amino acid in the H-chain was blocked and could not be determined by this method.

TABLE 2

N-terminal amino acid sequence of L chain of mouse anti-human IgE antibody

| Antibody | Amino acid sequence |
| --- | --- |
| 3A11A3C | Asp—Ile—Val—Leu—Thr—Gln—Ser—Pro—Ala—Ser—Leu—Ala—Val—Ser—Leu—Gly—Gln |
| 7D7C1C | Asp—Ile—Val—Leu—Thr—Gln—Ser—Pro—Ala—Ser—Leu—Ala—Val—Ser—Leu—Gly—Gln—Arg—Ala—Thr—Ile—Ser |
| 9D5C4H | Asp—Val—Val—Met—Thr—Gln—Thr—Pro—Leu—Ser—Leu—Pro—Val—Ser—Leu—Gly—Asp—Gln—Ala |
| 11D10H4C | Asp—Val—Val—Met—Thr—Gln—Thr—Pro—Leu—Ser—Leu—Pro—Val—Ser—Leu—Gly—Asp—Gln—Ala—Ser |

Example 4

Biochemical Properties of the Monoclonal Antibodies

Four antibodies produced by the clones obtained by Example 1 were analyzed.

(1) Specificity of Monoclonal Antibodies.

The specificity of monoclonal antibodies was determined by ELISA method using a solidified IgE system. The ELISA analysis was performed by applying the system used for the previously mentioned screening of hybridomas. The solidified human antigens, IgE, IgG, IgM and IgA, were placed in a 96 well plate (Falcon Co., Ltd. ) at a concentration of two μg/ml and 100 μl/well each and allowed to stand still overnight at 4° C. 2% bovine serum albumin (BSA) was added to each well and allowed to stand one hr. at room temperature, then each well was washed with 10 mM phosphate buffer (pH 7.4)—0.15M NaCl (PBS) and used as an analytical plate.

Each antibody was dissolved in PBS at a concentration of 0.63 μg/ml and 100 μl each of the antibody solution was added to the well. The well was allowed to stand for two hrs. and washed three times with PBS-0.05% Tween20 (PBS-Tween). 100 μl/well of peroxidase-labeled goat anti-mouse immunoglobulin (MBL Co., Ltd.) was added and incubated for two hrs. at room temperature. The well was washed three times with PBS-Tween and added 200 μl /well each of a mixed solution of 20 ml of 0.1M sodium acetate-0.05M sodium dihydrogenphosphate buffer, 1.0 ml of 40 mM ABTS (2,2'-azino-di-(3-ethylbenzothiazolin sulfonate) and 0.2 ml of 0.25M hydrogen peroxide solution, prepared just before the addition, as a substrate for the determination of enzyme activity and incubated at room temperature. After the reaction, the absorbance at 405 nm was measured with the ImmunoReader N J-2000 (Nippon InterMed Co. Ltd.).

The results are shown in FIG. 1. All antibodies selectively reacted only to IgE.

(2) The Affinity of Monoclonal Antibodies to IgE Antibody.

Figure 2:
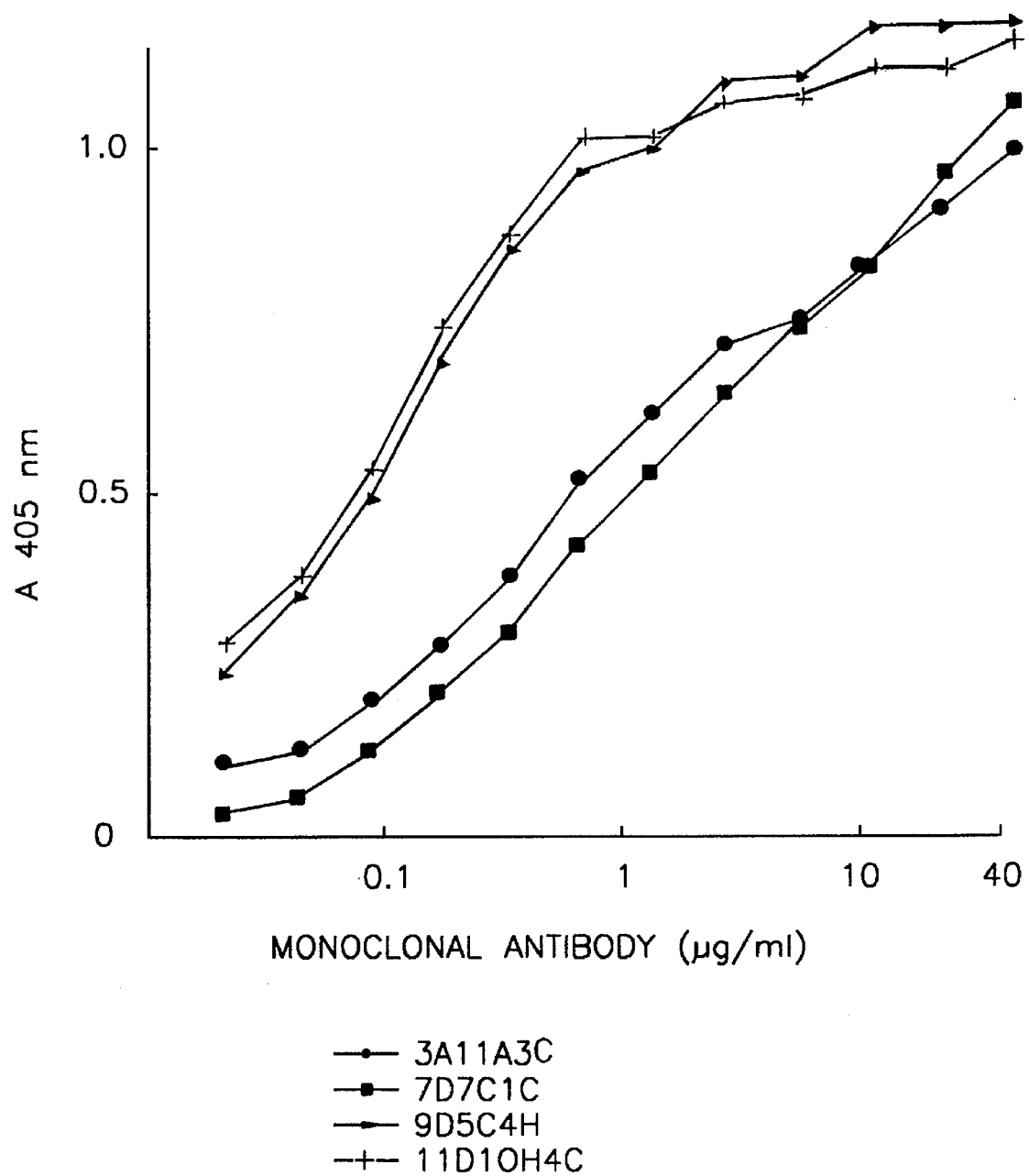
FIG. 2 shows the binding of monoclonal antibodies of the present invention to IgE.

In the determination mentioned above, the binding affinity to human IgE antibody was determined similarly in various concentrations of antibody. The results are shown in FIG. 2. Absorbance increased with the elevated concentration of added monoclonal antibodies and 9D5C4H showed the highest binding affinity.

(3) Binding to IgE-producing Human Myeloma Cells

IgE-producing human myeloma cells SKO-007 (ATCC CRL8033) were suspended in RPMI-1640 medium containing 10% FCS at a concentration of $2.5 \times 10^6$ cells/ml and two ml each of the suspension was placed in a 96 U-shaped well microplate (Falcon Co., Ltd.) and allowed to stand for one hr. at room temperature. The supernatant was removed, 0.1 ml (37 μg) each of antibody was added and caused to react for two hrs. at room temperature. The cells were washed three times with PBS and 100 μl/well of peroxidase-labeled goat anti-mouse immunoglobulin (MBL Co., Ltd. was added and incubated for two hrs. at room temperature. The cells were washed three times with PBS-Tween and added 200 μl/well each of a mixed solution of 20 ml of 0.1M sodium acetate-0.05M sodium dihydrogenphosphate buffer, 1.0 ml of 40 mM ABTS (2,2'-azino-di-(3-ethylbenzothiazolin sulfonate) and 0.2 ml of 0.25M hydrogen peroxide solution as a substrate prepared just before the addition and incubated at room temperature. After the reaction, cell free supernatant was transferred to a new plate and the absorbance at 405 nm was measured with the ImmunoReader NJ-2000 (Nippon InterMed Co. Ltd.).

Figure 4:
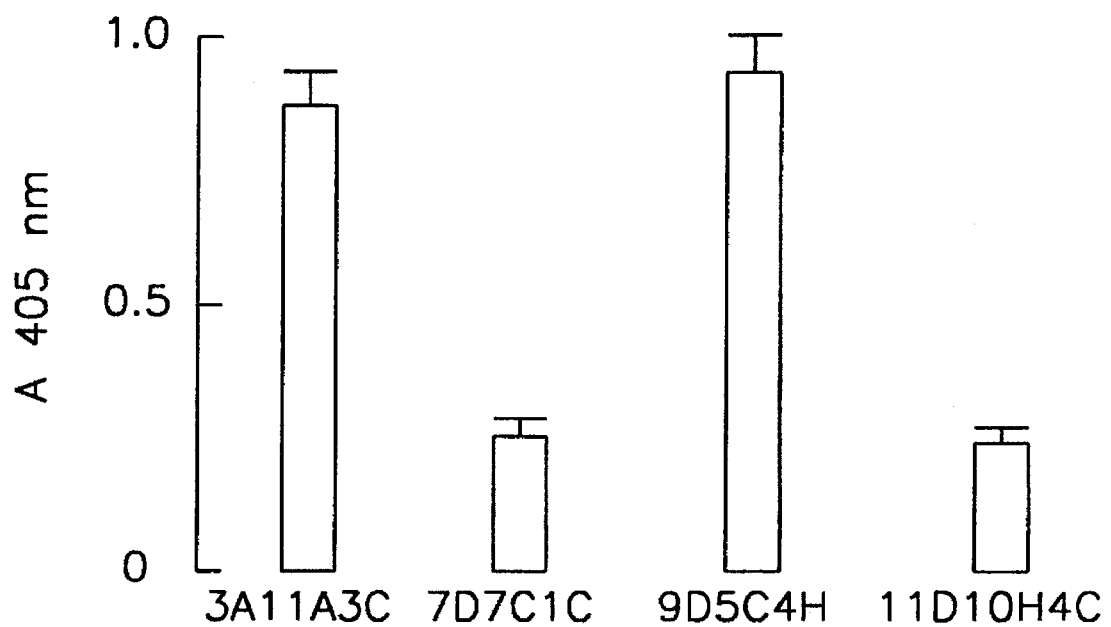
FIG. 4 shows the binding to the IgE-producing B cells.

The difference between the measured absorbances and those of control groups without antibody treatment are shown in FIG. 4. The all antibodies responded to IgE-producing B cells, particularly 3A11A3C and 9D5C4H exhibited high binding activity.

The antibodies of the present invention clearly recognized IgE expressed on the surface of B cells.

(4) Recognition Site of Antigen by Anti-human IgE antibody.

The antibodies of the present invention were tested to determine whether they recognize Fab or Fc of human IgE antibody. The binding inhibition of mouse anti-human IgE antibody to solidified IgE was rested with a sheep antibody which recognizes Fc region of of IgE.

Figure 3:
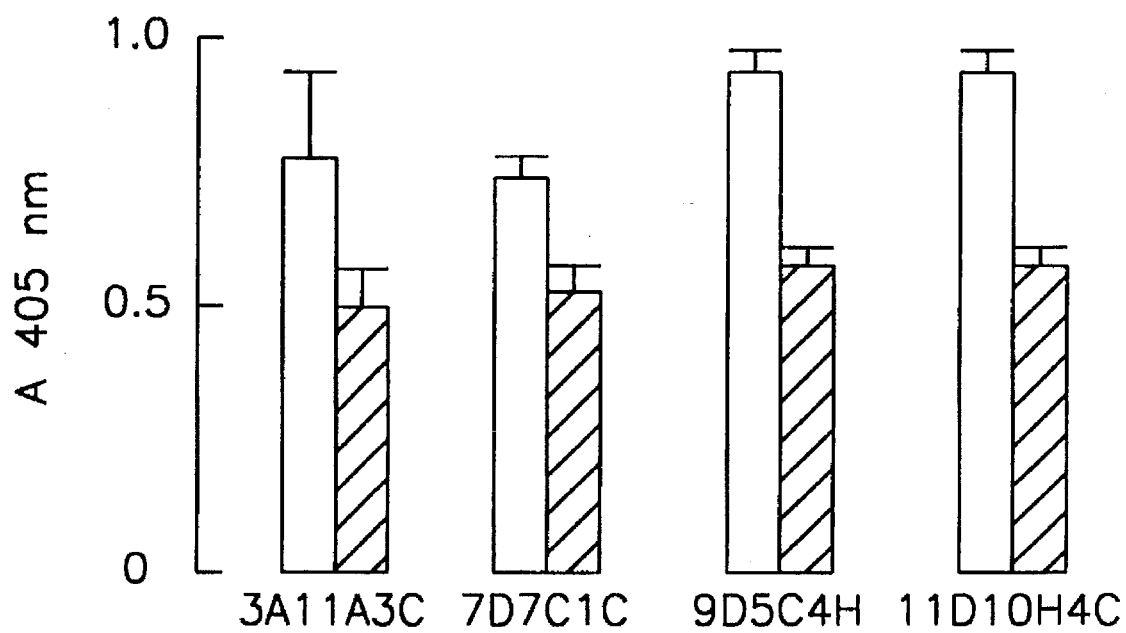
FIG. 3 shows the binding inhibition of monoclonal antibodies to IgE by sheep anti-human IgE (Fc) antibody. The striped bars show the treatment with anti-human IgE (Fc) antibody.

To human IgE immobilized well, a one thousand-fold diluted sheep anti-human IgE (Fc) antibody (Serotech Co., Ltd.) was added and incubated for 2.5 hrs. at room temperature to block Fc region of IgE. The wells were washed three times with PBS-Tween, 0.1 ml each of antibody of the present invention was added at a concentration of 10 μg/ml and incubated for two hrs. at room temperature. The wells were washed three times with PBS and 200 μl/well each of a mixed solution of 20 ml of 0.1M sodium acetate-0.05M sodium dihydrogenphosphate buffer, 1.0 ml of 40 mM ABTS (2,2'-azino-di-(3-ethylbenzothiazolin-sulfonate) and 0.2 ml of 0.25M hydrogen peroxide solution as a substrate for the determination of enzyme activity and incubated at room temperature. After incubation, the reaction mixture was transferred to a new plate and the absorbance at 405 nm was determined with the ImmunoReader N J-2000 (Nippon InterMed Co. Ltd.) and compared with that of control group without sheep anti-human IgE (Fc) antibody treatment. The results are shown in FIG. 3. All antibodies showed comparatively low binding to IgE coated well pre-treated with sheep anti-human IgE antibody compared with those of untreated control group indicating the antibody binding site at isolated in Fc region of IgE.

(5) Analysis of Recognition Site of Antigen by Antibodies of the Present Invention Using IgE Coated CD23 Positive Human Cells.

IM-9 cells are known as cells expressing Fcε receptor on cell surface. The cells were deposited as ATCC CCL159 and is publicly available. The cells bind IgE through cell surface receptors. The antibodies of the present invention recognize Fc region as shown in the above mentioned (4). Fcε receptor binding site existing in the Fc region was further investigated in detail.

In one ml of PBS containing 0.3% BSA and 0.02% NaN$_3$, $5\times10^6$ cells of IM-9 were suspended, 20 μg of human IgE was added and incubated for one hr. at 4° C. The treated cells were washed three times with the solution shown above, cell numbers were counted and $0.7\times10^6$ cells were incubated with 50 μg of anti-human IgE antibodies of the present invention for one hr. at 4° C. The cells were washed three times by a similar manner, FITC-labeled goat anti-mouse IgG antibody (Nichirei K.K.) was added and stained for 30 min. at 4° C. After staining, cells were washed and stained cells were analyzed with a flow cytometry (Cyto ACE-150, JASCO Co., Ltd.). The percentage of stained cells in the total cells are shown in Table 3.

As shown in Table 3, IM-9 cells were stained by the addition of the antibodies of the present invention. This indicates the antibodies of the present invention recognize IgE antibody bound to Fcε receptor as well as Fc region of IgE antibody as shown in (4). Thus, it is confirmed that the antibodies of the present invention recognize Fc region of IgE other than Fcε receptor binding site. No antibody having such characteristic feature has been known.

TABLE 3

| Results of cell staining | |
|---|---|
| Mouse anti-human IgE antibody | Stained cells (%) |
| Without addition | 0.1 |
| 3A11A3C | 12.0 |
| 7D7C1C | 5.5 |
| 9D5C4H | 11.6 |
| 11D10H4C | 11.0 |

(6) Determination of Histamine Release From Human and Canine Peripheral Basophils Induced by Monoclonal Antibody.

The receptor to human IgE antibody present on the surfaces of mast cells and basophils in human and canine peripheral blood mononuclear cell (PBMC) fractions. The binding of antigen to IgE antibody bound to Fcε receptor or the formation of crosslinkage between IgE antibodies by anti-IgE antibody induces release of chemical mediators such as histamine from these cells. The treatment of these cells with the antibodies of the present invention inhibits the histamine release from the cells and competitively works to IgE antibody bound to cell surface and to release antibody from receptor.

Figure 5:
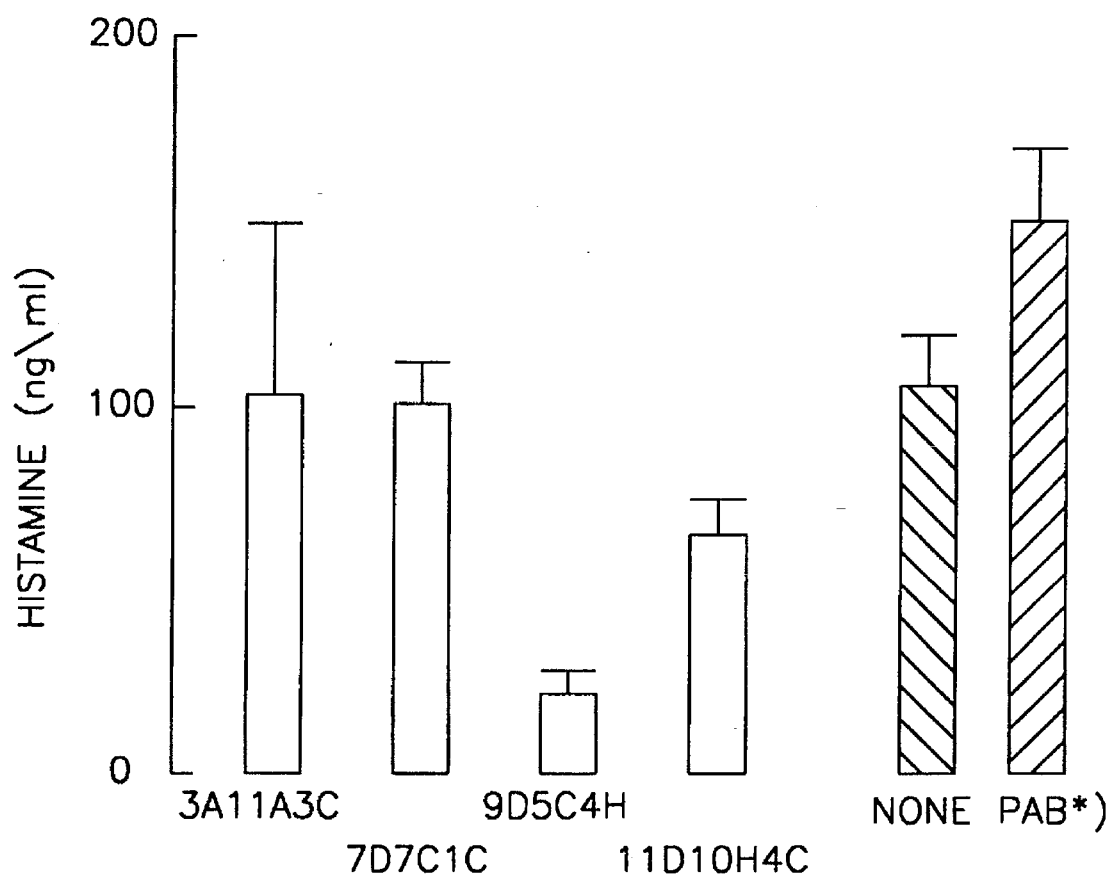
FIG. 5 shows the histamine release test results from human peripheral basophils. Symbols, None and PAB, in the Fig. represent non-treated cell with antibody and anti-IgE polyclonal antibody treated cells, respectively.
Figure 6:
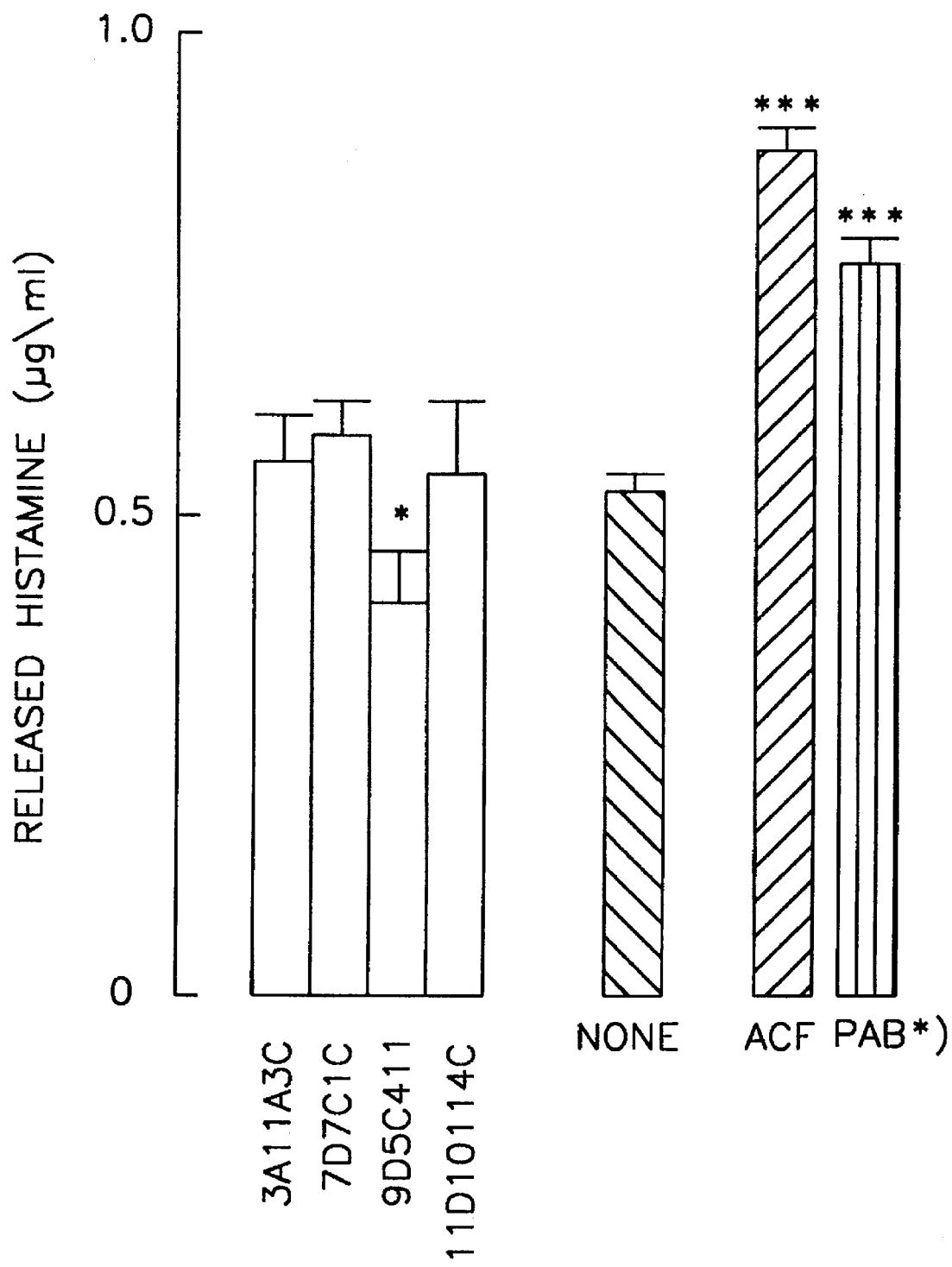
FIG. 6 shows the histamine release test results from canine peripheral basophils. Symbols, None, ACF and PAB, in the Fig. represent non-treated cell with antibody, anti-human IgE (Fab) monoclonal antibody treated cells and anti-IgE polyclonal antibody treated cells, respectively.

Heparin added peripheral blood samples were drawn from human and dog, diluted 2-fold with PBS and mononuclear cells (PBMC) were separated by centrifugation technique using Lymphosepar (IBL Co., Ltd.). PBMC were washed three times with RPMI-1640 containing 10% FCS and about $1\times10^5$ cells were treated with human IgE antibody to saturate cell surface receptors. To the cells, 10 μg of the antibodies of the present invention were added and incubated for 30 min. at 37° C., then released histamine was determined using HRT kit (Miles Co., Ltd.). Control histamine release groups were obtained by treatment with commercial goat anti-human IgE polyclonal antibody (PAB) (MBL Co., Ltd.) and by treatment with monoclonal antibody (ACF) recognizing Fab domain of human IgE antibody and the results are shown in FIG. 5 and 6, respectively. The antibodies of the present invention did not induce histamine release from treated cells, but dissociated Fcε receptor bound IgE antibody from human cells (FIG. 5). ACF is an antibody recognizing Fab portion of IgE obtained by the screening shown above (4).

(7) Release Inhibitory Effect of Histamine Release From Canine Basophils by Anti-human IgE Antibody.

Figure 7:
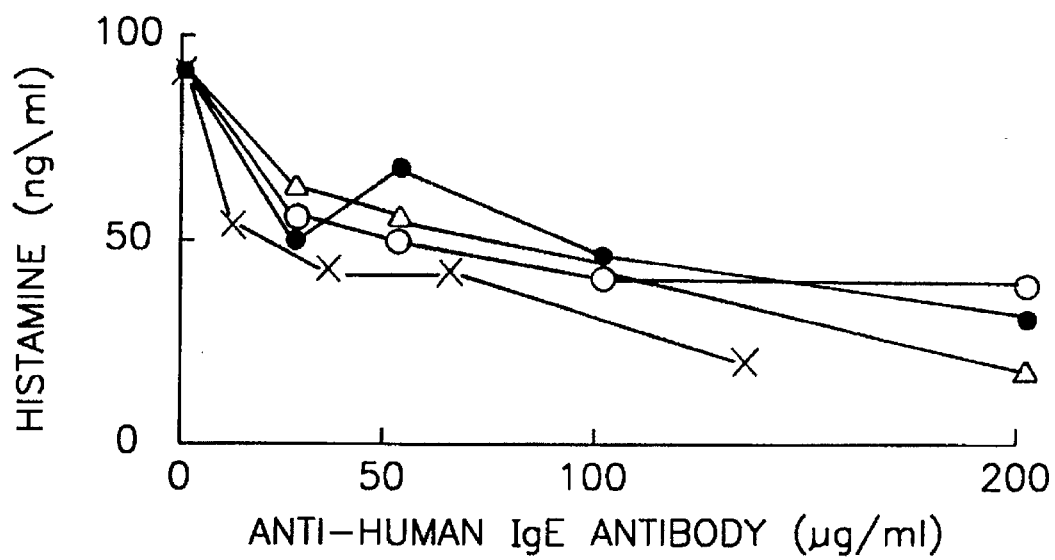
FIG. 7 shows the histamine release inhibitory test from canine peripheral basophils.

Heparin added peripheral blood was drawn from a healthy dog, diluted 2-fold with PBS, layered on Lymphosepar (IBL Co., Ltd.) and centrifuged for 15 min. at 2,000 rpm to isolate cells in the intermediate layer as peripheral basophil mononuclear cell (PBMC) fraction. The fraction was washed three times with RPMI-1640 medium containing 10% FCS, suspended to make about $1\times10^6$ cells/ml and put 50 μl each into a 96 well microtiter plate. 50 μl each of varying concentrations of anti-human IgE antibody was added, incubated for 30 min. at 37° C. and released histamine was determined. Inhibitory activity of histamine release by antibodies are shown in FIG. 7. All antibodies inhibited histamine release in a dose-dependent manner.

Inhibition of histamine release from basophils by the antibodies of the present invention was confirmed.

(8) Expulsion of Receptor Bound IgE by Anti-human IgE Antibody.

Canine peripheral blood mononuclear cell (PBMC) fraction was treated by a similar manner shown in (7). The cells were suspended in RPMI-1640 medium to make $1\times10^6$ cells/ml, and distributed 50 μl each to a 96 well microtiter plate. 100 μg/ml of anti-human IgE antibodies of the present invention were added and incubated for 30 min. at 37° C. Then, 500 μg/ml of a monoclonal antibody (ACF) which recognizes Fab portion of IgE antibody was added to induce histamine release for 30 min. at 37° C., and released histamine was determined. The control group was made without addition of the antibodies not to induce dissociation of IgE. The results are shown in Table 4.

Cells incubated with mouse anti-human IgE antibody were further treated by the condition to induce IgE-dependent histamine release (ACF antibody treatment). The treated cells showed decrease of histamine release in comparison with those of anti-human IgE antibody untreated cells. Inhibition of histamine release induced by IgE crosslinkage suggests dissociation of IgE from Fcε receptor.

TABLE 4

| Results of histamine release from canine pBMC | | |
|---|---|---|
| Mouse anti-human IgE antibody | Control | Addition of ACF |
| No addition | 6.2 ± 1.0 | 73.4 ± 4.3 |
| 3A11A3C | 5.4 ± 0.8 | 45.2 ± 9.8* |
| 7D7C1C | 5.0 ± 0.4 | 51.5 ± 6.5* |
| 9D5C4H | 7.6 ± 3.4 | 61.9 ± 3.8* |
| 11D10H4C | 6.3 ± 0.5 | 62.8 ± 3.4 |

Unit: ng/ml
*: significant to no addition of antibody at a level of 5%.

The present invention provides anti-IgE antibodies recognize IgE bound to Fcε receptor and also do not induce histamine release from IgE-pretreated human peripheral blood basophils. The antibodies provided by the present invention dissociate IgE antibody bound to basophil surface and inhibit histamine release caused by antigen stimulation. Furthermore, the monoclonal antibody has a specified N-terminal amino acid sequence of L-chain and clearly different from known antibodies.

The antibody of the present invention can be used for medicine, diagnostic drug and reagent.

---

We claim:
1. Monoclonal antibodies:
1) which bind to immunoglobulin E (IgE) bound to human mast cells or basophils or CD23-positive cells, which bind to IgE bound Fc receptor on human mast cells, basophils or CD23-positive cells, which dissociate IgE antibody from Fc receptor on human mast cells, basophils or CD23-positive cells, which bind to IgE bound to Fc receptor without inducing the release of chemical mediators,
2) which have a molecular weight of about 150,000 daltons (as determined by SDS-PAGE; non-reduced state), and which
3) bind to human IgE-producing B cells.

* * * * *